United States Patent [19]

Slusarchyk et al.

[11] 4,252,973

[45] Feb. 24, 1981

[54] PROCESS FOR CHEMICALLY REMOVING THE ACYL SIDECHAIN FROM CEPHALOSPORINS AND PENICILLINS

[75] Inventors: William A. Slusarchyk, Belle Mead; Christopher M. Cimarusti, Hamilton, both of N.J.

[73] Assignee: E. R. Squibb & Sons, Inc., Princeton, N.J.

[21] Appl. No.: 55,250

[22] Filed: Jul. 6, 1979

[51] Int. Cl.³ .......................................... C07D 501/02
[52] U.S. Cl. ...................................... 544/21; 548/190; 544/27; 544/26; 544/30; 260/245.2 R
[58] Field of Search .................... 544/27, 26, 21, 30; 260/239.1, 245.2; 548/190

[56] References Cited

U.S. PATENT DOCUMENTS

| | | | |
|---|---|---|---|
| 3,499,909 | 3/1970 | Weissenburger et al. | 260/306.7 |
| 3,549,628 | 12/1970 | Chauvette | 260/243 |
| 3,573,295 | 3/1971 | Johnson et al. | 260/243 |
| 3,573,296 | 3/1971 | Johnson et al. | 260/243 |
| 3,575,970 | 4/1971 | Weissenburger et al. | 260/306.7 |
| 3,697,515 | 10/1972 | Fechtig et al. | 260/243 C |
| 3,840,532 | 10/1974 | Hayes et al. | 260/243 C |
| 3,875,151 | 4/1975 | Fechtig et al. | 260/243 C |
| 3,920,638 | 11/1975 | Bickel et al. | 260/243 C |
| 3,932,392 | 1/1976 | Johnson et al. | 260/243 C |
| 4,031,087 | 6/1977 | Karady et al. | 260/243 C |
| 4,068,071 | 1/1978 | Tsushima et al. | 544/19 |
| 4,068,072 | 1/1978 | Tsushima et al. | 544/19 |

FOREIGN PATENT DOCUMENTS 788750  9/1972  Belgium .

OTHER PUBLICATIONS

Kardy et al., Tetrahedron Letters, No. 5, pp. 407–408, (1978).
Lunn et al., Tetrahedron Letters, No. 14, pp. 1307–1310, (1974).
Busko–Oszczapowicz et al., Rocznik, Chemii Ann. Soc. Chim. Polonorum, vol. 48, pp. 253–261, (1974).
Shimizu et al., Chem. Phar. Bull., vol. 24, pp. 2629–2636, (1976).
Shiozaki et al., J.C.S. Chem. Comm., pp. 517–518, (1978).

*Primary Examiner*—Nicholas S. Rizzo
*Attorney, Agent, or Firm*—Lawrence S. Levinson; Dale Lovercheck; Stephen B. Davis

[57] ABSTRACT

A process for removing the acyl sidechain from penicillins and cephalosporins which comprises chlorinating the acyl compound and treating the resulting iminochloride with an o-aminothiophenol to obtain the corresponding 6$\beta$-aminopenicillin or 7$\beta$-aminocephalosporin.

27 Claims, No Drawings

PROCESS FOR CHEMICALLY REMOVING THE ACYL SIDECHAIN FROM CEPHALOSPORINS AND PENICILLINS

BACKGROUND OF THE INVENTION

Various 7β-amino cephalosporins and 6β-amino penicillins including those having a 7α- or 6α-methoxy substituents are employed as starting materials in the preparation of semi-synthetic cephalosporins and penicillins. These 7β-amino cephalosporins and 6β-amino penicillins are for economic reasons prepared by removing the acyl sidechain from cephalosporins and penicillins that are obtained by fermentation processes. Both chemical and enzymatic processes have been employed to accomplish this deacylation.

For example Weissenburger et al. U.S. Pat. Nos. 3,499,909 and 3,575,970 disclose deacylation processes in which the acylated penicillin or cephalosporin is converted to a silyl ester, halogenated to form an iminohalide, reacted with an alcohol to form an iminoether, and then treated with water and a hydroxyl containing compound to remove the acyl sidechain.

Chauvette in U.S. Pat. No. 3,549,628 discloses preparing 7-ADCA by converting an acylated 7-ADCA ester to its iminohalide, treating with alcohol to form the iminoether, and hydrating to remove the acyl sidechain. Hayes et al. in U.S. Pat. No. 3,840,532 disclose a similar process in which particular solvent systems are employed.

Johnson et al. in U.S. Pat. Nos. 3,573,295 and 3,573,296 disclose process for removing the acyl sidechain from cephaloporin C which involve a silyl ester, halogenating, converting the iminohalide to an iminoether, and hydrolyzing. Johnson et al. in U.S. Pat. No. 3,932,392 disclose a deacylation process employing particular acid scavengers during the halogenating step.

Fechting et al. in U.S. Pat. Nos. 3,697,515 and 3,875,151 and Bickel et al. in U.S. Pat. No. 3,920,638 disclose deacylation processes which involve forming an iminohalide, converting the iminohalide to an iminoether, and hydrolyzing to remove the acyl sidechain.

Karady et al. in U.S. Pat. No. 4,031,086 and Tetrahedron Letters, No. 5, p. 407–408 (1978) disclose a process for chemically removing an acyl sidechain from a cephamycin type cephalosporin.

Lunn et al., Tetrahedron Letters, No. 14, p. 1307–1310 (1974), also disclose a process for chemically removing an acyl sidechain from a cephamycin type cephalosporin.

Tedeka in Belgian Patent No. 788,750 disclose a deacylation process wherein the cephalosporin is converted into an iminohalide, then treated to convert the iminohalide to a thioether, and then treated to remove the acyl sidechain.

Tsushima et al. in U.S. Pat. No. 4,068,071 describe a process for removing the acyl sidechain from penicillins and cephalosporins by first thioacylating, converting the thioacyl compound to a disulfide, and then removing the sidechain by solvolyzation. Tsushima et al. in U.S. Pat. No. 4,068,072 remove the acyl sidechain by converting the thioacyl derivative to a thiohalide and then removing the sidechain by solvolyzation.

Busko-Oszczapowicz et al., Roczniki Chemii Ann. Soc. Chim. Polonorum, Vol. 48, p. 253–261 (1974), disclose converting an acylated iminohalide penicillin to a diacyl penicillin followed by treatment with sodium thiophenolate to remove one of the acyl groups.

Shimizu et al., Chem. Pharm. Bull., Vol. 24, p. 2629–2636 (1976), disclose a selective deacylation process for cephamycin type cephalosporins.

Shiozaki et al., J.C.S. Chem. Comm.; p. 517–518 (1978) disclose a process for removing the acyl sidechain from cephamycin C.

SUMMARY OF THE INVENTION

This invention is directed to a process for removing the acyl sidechain from cephalosporins including 7α-methoxy cephalosporins which are known as cephamycins or from penicillins including 6α-methoxy penicillins. The cephalosporin or penicillin is first treated with a chlorinating agent. The resulting iminochloride is then treated with an o-amino thiophenol to yield the desired 7β-amino cephalosporin or 6β-amino penicillin.

DETAILED DESCRIPTION

In general, the starting acyl cephalosporins and penicillins employed in this process are those which are obtained by fermentative processes. In some cases, a chemical treatment step is employed in the fermentation media in order to aid in the separation of the desired starting material.

These acyl cephalosporins and penicillins can be represented by the formula

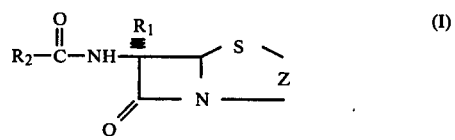

wherein Z is

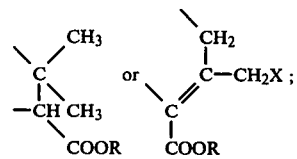

R is a readily removable carboxy protecting group; $R_1$ is in the α-configuration and is hydrogen or methoxy; X is hydrogen,

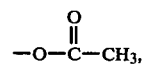

or —S—hetero; $R_2$ is straight or branched chain lower alkyl of 1 to 4 carbons, benzyl, phenoxymethyl, —(CH$_2$)$_3$—COOR,

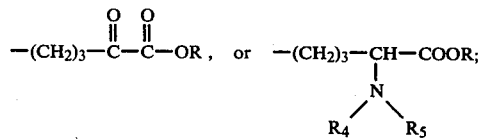

and $R_4$ is hydrogen and $R_5$ is an amino protecting group or $R_4$ and $R_5$ taken together with the N-atom form an imido group such as succinimido or phthalimido.

According to this invention the compound of formula I is chlorinated to obtain the iminochloride of the formula

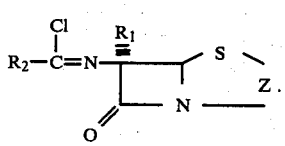 (II)

Suitable chlorinating agents include phosgene and phosphorus pentachloride and this reaction is performed according to known procedures as note for example Karady et al., Lunn et al., etc., referred to above.

The iminochloride of formula II is then treated with an equimolar or molar excess of the o-amino thiophenol of the formula

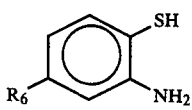 (III)

wherein $R_6$ is hydrogen, nitro, chloro or bromo, preferably hydrogen, to yield the benzothiazole of the formula

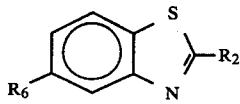 (IV)

and the desired 6β-amino penicillin or 7β-amino cephalosporin of the formula

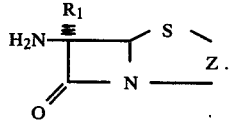 (V)

The reaction between the iminochloride of formula II and the o-amino thiophenol of formula III is carried out in a suitable organic solvent such as, for example, dichloromethane, chloroform, 1,2-dichloroethane, toluene, benzene, acetonitrile, ethylacetate, dimethoxyethane, tetrahydrofuran, dioxane, etc., at a temperature of from about −35° C. to about 35° C. and in the presence of from about 1 to about 3 molar equivalents of an organic base such as, for example, pyridine, N,N-dimethylaniline, N,N-diethylaniline, etc. The reaction will take from about 15 minutes to about 4 hours. The resulting reaction products, i.e., the benzothiazole of formula IV and the 6β-amino penicillin or 7β-amino cephalosporin of formula V, are separated by conventional techniques such as, for example, column chromatography.

The compounds of formula V are, of course, valuable as intermediates which can then be acylated so as to yield various antibacterially active penicillins and cephalosporins. The carboxy protecting group R can be removed after the acylation reaction. Also, in the case of the cephalosporins wherein X is

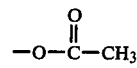

other groups can be introduced at this position of the cephalosporin nucleus by known reactions.

The carboxy protecting group represented by the symbol R in the preceding formulas include, for example, straight or branched chain lower alkyl of 1 to 4 carbons, benzyl, p-nitrobenzyl, p-methoxybenzyl, benzhydryl, 2,2,2-trichloroethyl, —Si(CH$_3$)$_3$,

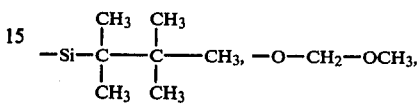

wherein $R_7$ is hydrogen, chloro, or bromo,

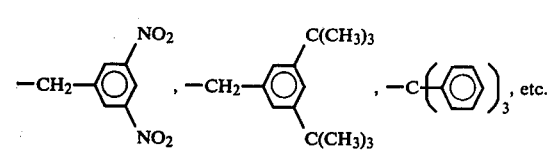

The term hetero as used in the definition of the symbol X in the preceding formulas includes unsubstituted or substituted 5- or 6-membered rings having one or more N, O, or S atoms, as for example,

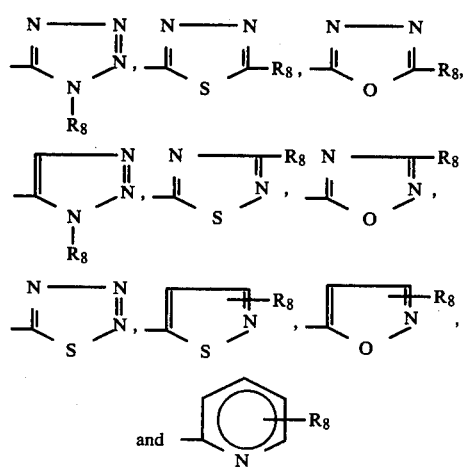

wherein $R_8$ is hydrogen or straight or branched chain lower alkyl of 1 to 4 carbons, especially methyl.

The cephalosporins of formula I wherein X is —S—hetero are obtained by a displacement reaction of the corresponding 3-acetoxymethyl or 3-carbamoyloxymethyl cephalosporin. Thus, when $R_1$ is hydrogen, cephalosporin C can be treated with a molar excess of the thiol of the formula H—S—hetero        (VI)

to yield the desired 3-heterothiomethyl cephalosporin starting material. Similarly, when $R_1$ is methoxy, cephamycin C can be treated with a molar excess of the thiol of formula VI to yield the desired 3-heterothiomethyl cephamycin starting material.

The amino protecting group represented by the symbol $R_5$ in the preceding formulas includes

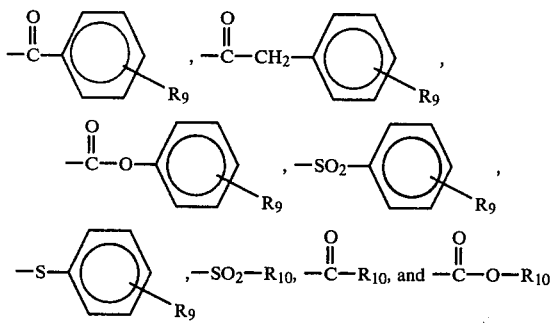

wherein $R_9$ is hydrogen, methyl, methoxy, nitro, or chloro and $R_{10}$ is straight or branched chain lower alkyl of 1 to 4 atoms or such lower alkyl substituted with from 1 to 3 chloro groups, i.e, chloromethyl, 2,2,2-trichloroethyl, etc.

The following examples are illustrative of the invention. All temperatures are on the centigrade scale.

EXAMPLE 1

7β-Amino-7α-methoxy-3-[[(1-methyl-1H-tetrazol-5-yl)thio]methyl]-3-cephem-4-carboxylic Acid Benzhydryl Ester from 7β-(D-5-tert-Butoxycarbonylamino-5-carboxyvaleramido)-7α-methoxy-3-[[(1-methyl-1H-tetrazol-5-yl)thio]methyl]-3-cephem-4-carboxylic Acid Dibenzhydryl Ester To a solution of 467 mg. (0.5 mmol.) of 7β-(D-5-tert-butoxycarbonylamino-5-carboxyvaleramido)-7α-methoxy-3-[[(1-methyl-1H-tetrazol-5-yl)thio]methyl]-3-cephem-4-carboxylic acid dibenzhydryl ester [prepared as taught by Shimizu et al., Chem. Pharm. Bull. 24, p. 2629–2636 (1976)] and 121 μl. (1.5 mmol.) of pyridine in 6 ml. of dry dichloromethane at 25° under nitrogen is added 0.63 ml. of 12.5% phosgene in benzene (0.525 mmol.). The mixture is stirred at 25° for 3.5 hours and diluted with 5% aqueous sodium bicarbonate solution and dichloromethane to adjust the pH to 7.5–8.0. The dichloromethane layer is washed with 5% sodium bicarbonate, dried (MgSO$_4$), and evaporated in vacuo to a residue, which is dried further by two evaporations in vacuo from dry benzene to give 430 mg. (90% yield) of imino chloride; pmr (CD$_2$Cl$_2$) δ 2.73 (2H, t, CH$_2$—C=N), 3.48 (3H, s, OCH$_3$), 3.77 (3H, s, N—CH$_3$) 5.00 (1H, s, C—6).

To a stirred solution of 375 mg. (0.39 mmol.) of the above mentioned imino chloride and 63 μl. (0.78 mmol.) of dry pyridine in 6 ml. of dry dichloromethane at 25° under nitrogen is added 82 μl. (0.78 mmol) is o-aminothiophenol. The mixture is stirred for 1.3 hours and diluted with aqueous sodium bicarbonate solution and dichloromethane. The dichloromethane layer is washed with water, dried (Na$_2$SO$_4$) and evaporated in vacuo to give the desired product. Purification by preparative thin layer chromatography on silica gel using dichloromethane-ethyl-acetate (9:1) affords 51 mg. of 7β-amino-7α-methoxy-3-[[(1-methyl-1H-tetrazol-5-yl)thio]methyl]-3-cephem-4-carboxylic acid benzhydryl ester; pmr (DCCl$_3$) δ 3.52 (3H, s, OCH$_3$), 3.83 (3H, s, NCH$_3$), 4.40 (2H, q, J=13 Hz, C'-3), 4.87 (1H, s, C-6), and 74 mg. of D-2-tert-butoxycarbonylamino-5-[benzothiazol-2-yl]pentanoic acid benzhydryl ester; pmr (DCCl$_3$) δ 1.43 (9H, s, t-Bu), 1.93 (4H, m, CH$_2$—CH$_2$), 3.07 (2H, m, CH$_2$), 4.47 (1H, m, CH), 5.20 (1H, d, J=8 Hz, NH), 6.92 (1H, s, COOCH), 7.3–8.2 (14H, complex, aromatics).

EXAMPLE 2

7β-Amino-7α-methoxy-3-[[(1-methyl-1H-tetrazol-5-yl)thio]methyl]-3-cephem-4-carboxylic Acid Benzhydryl Ester from 7β-butyramido-7α-methoxy-3-[[(1-methyl-1H-tetrazol-5-yl)thio]methyl]-3-cephem-4-carboxylic Acid Benzhydryl Ester Treatment of 396 mg. (0.66 mmol.) of 7β-butyramido-7α-methoxy-3-[[(1-methyl-1H-tetrazol-5-yl)thio]methyl]-3-cephem-4-carboxylic acid benzhydryl ester in 8 ml. of dry dichloromethane with 162 μl. (2 mmol.) of dry pyridine and 0.84 ml. of 12.5% phosgene in benzene according to the procedure for preparation of the imino chloride in Example 1 provides 375 mg. of the desired imino chloride; pmr (DCCl$_3$) δ 2.75 (2H, t, CH$_2$—C=N), 3.58 (3H, s, OCH$_3$), 3.83 (3H, s, NCH$_3$), 5.03 (1H, s, C-6).

Treatment of 470 mg. (0.76 mmol.) of this imino chloride in 10 ml. of dry dichloromethane with 120 μl. of dry pyridine and 159 μl. (1.51 mmol.) of o-aminothiophenol for 1 hour according to the procedure of Example 1 provides, after purification by preparative thin layer chromatography on silica gel using dichloromethane-ethyl acetate (9:1), 73 mg. of 7β-amino-7α-methoxy-3-[[(1-methyl-1H-tetrazol-5-yl)thio[methyl]-3-cephem-4-carboxylic acid benzhydryl ester (Rf ~ 0.4) and 2-propylbenzothiazole (R$_f$ ~ 0.9); pmr (DCCl$_3$) δ 1.03 (3H, s, CH$_3$), 1.92 (2H, sextet, CH$_2$), 3.27 (2H, t, CH$_2$—C=N), 7.0–8.2 (4H, m, aromatics).

EXAMPLE 3

7β-Amino-3-methyl-Δ$^3$-cephem-4-carboxylic acid 2,2,2-Trichloroethyl Ester from 7β-Phenylacetamido-3-methyl-Δ$^3$-cephem-4-carboxylic Acid 2,2,2-Trichloroethyl Ester Treatment of 300 mg. (0.65 mmol.) of 7β-phenylacetamido-3-methyl-Δ$^3$-cephem-4-carboxylic acid 2,2,2-trichloroethyl ester in 5 ml. of dry dichloromethane with 166 μl. (1.93 mmol) of dry pyridine and 0.80 ml. of 12.5% phosgene in benzene according to the procedure in Example 1 provides 296 mg. of imino chloride intermediate; IR (CHCl$_3$) 1788 (β-lactam), 1740 (ester C=O), and 1680 (C=N) cm$^{-1}$.

Treatment of this imino chloride (296 mg., 0.62 mmol.) in 10 ml. of dry dichloromethane with 2 mmol. of dry pyridine and 2 mmol. of o-aminothiophenol according to the procedure of Example 1 provides 39 mg. of 7β-amino-3-methyl-Δ$^3$-cephem-4-carboxylic acid 2,2,2-trichloroethyl ester after preparative thin layer chromatography on silica gel using dichloromethane-ethyl acetate (9:1).

EXAMPLE 4

7β-Amino-3-methyl-Δ³-cephem-4-carboxylic Acid from 7β-Phenylacetamido-3-methyl-Δ³-cephem-4-carboxylic Acid Trimethylsilyl Ester Pyridine (3 mmol.) is added to a suspension of 1 mmol. of 7β-phenylacetamido-3-methyl-Δ³-cephem-4-carboxylic acid potassium salt in 8 ml. of dry dichloromethane at 0°. Trimethylsilyl chloride (1 mmol.) is added and the mixture is stirred for 30 minutes. A solution of 12.5% phosgene in benzene (1.26 ml., 1.5 mmol.) is added to the above trimethylsilyl ester mixture, and the resulting reaction mixture is stirred at 0° for 2 hours. The solvents are removed in vacuo and 6 ml. of dry dichloromethane is added to the residue. Pyridine (2 mmol.) is added followed by 2 mmol. of o-aminothiophenol. The mixture is stirred for 2 hours at 0° and then aqueous sodium bicarbonate solution and dichloromethane are added to adjust the pH to 7.5–8.0. The aqueous layer is washed twice with ethyl acetate, cooled in an ice-water bath, and acidified to pH 4. The resulting precipitate is collected, washed with acetone:water (1:1) and then acetone, and then dried to give the desired product 7β-amino-3-methyl-Δ³-cephem-4-carboxylic acid.

EXAMPLE 5

7β-Amino-7α-methoxy-3-acetoxymethyl-3-cephem-4-carboxylic acid, t-butyl ester from 7β-phenylacetamido-7α-methoxy-3-acetoxymethyl-3-cephem-4-carboxylic acid, t-butyl ester Treatment of 7β-phenylacetamido-7α-methoxy-3-acetoxymethyl-3-cephem-4-carboxylic acid, t-butyl ester (1 mmol.) in 8 ml. of dry dichloromethane with 0.24 ml. (3 mmol.) of dry pyridine and 1.26 ml. (1.5 mmol.) of 12.5% phosgene in benzene according to the procedure of Example 1 yields the desired imino chloride intermediate as a residue.

Treatment of a solution of this imino chloride (0.5 mmol.) in 6 ml. of dry dichloromethane with 81 μl. (1 mmol.) of dry pyridine and o-aminothiophenol (1 mmol) according to the procedure of Example 1 provides 7β-amino-7α-methoxy-3-acetoxymethyl-3-cephem-4-carboxylic acid, t-butyl ester as a residue after purification by chromatography on silica gel.

EXAMPLE 6

6β-Aminopenicillanic Acid 2,2,2-trichloroethyl ester from 6β-phenylacetamisopenicillanic acid 2,2,2-trichloroethyl ester Dry pyridine (6.45 mmol.) and then 2.68 ml. of 12% phosgene in benzene is added to a solution of 1.00 g. (2.15 mmol.) of 6β-phenylacetamidopenicillanic acid 2,2,2-trichloroethyl ester in 15 ml. of dry dichloromethane at 25° under nitrogen. After standing for 1.25 hours, the mixture is diluted with aqueous sodium bicarbonate solution and brought to pH 7.5–8.0. After extracting with dichloromethane, the dichloromethane extract is dried (MgSO₄), and evaporated to give 1.10 g. of imino chloride intermediate; IR (CHCl₃) 1780 (β-lactam C=O), 1760 (ester C=O), and 1680 (C=N) cm⁻¹.

To a solution of this imino chloride (562 mg., 1.16 mmol.) in 10 ml. of dry dichloromethane under N₂ at 25° is added 0.24 ml. (3.0 mmol.) of dry pyridine followed by 0.186 ml. of o-aminothiophenol. The mixture is stirred for 1.5 hours, after which time, thin layer chromatography on silica gel using dichloromethane-ethyl acetate (9:1) indicates no starting material but instead 6β-aminopenicillanic acid 2,2,2-trichloroethyl ester (R$_f$~0.3) and a mixture of o-aminothiophenol and 2-benzyl benzothiazole (R$_f$~0.9-0.95). The mixture is diluted with aqueous sodium bicarbonate solution and dichloromethane. The dichloromethane layer is washed with water, dried (MgSO₄) and evaporated to a residue (679 mg.) consisting of about equivalent amounts of 6β-aminopenicillanic acid 2,2,2-trichloroethyl ester and 2-benzyl benzothiazole, and some o-aminothiophenol; pmr (DCCl₃) ~ 1.60, 1.73 (6H, two singlets C(CH₃)₂), 4.57 (1H, s, C-3), 4.67 (1H, d, J=4.5 Hz, C-6), 5.57 (1H, d, J=4.5 Hz, C-5) and 4.45 (2H, s, CH₂ of 2-benzyl benzothiazole).

EXAMPLE 7

6β-Aminopenicillanic Acid from 6β-Phenylacetamidopenicillanic Acid Trimethylsilyl Ester To a suspension of 6β-phenylacetamidopenicillanic acid potassium salt (1 mmol.) and N,N-dimethylaniline (3 mmol.) in 6 ml. of dry methylene chloride under nitrogen at 0° there is added 1 mmol. of trimethylsilyl chloride. The mixture is stirred for 30 minutes. Then a solution of 1.26 ml. of 12.5% phosgene in benzene is added to the above trimethylsilyl ester mixture. This reaction mixture is stirred at 0° for 2 hours and then the solvents are removed in vacuo. Fresh dichloromethane (6 ml.) is added followed by 2 mmol. of N,N-dimethylaniline and then 2 mmol. of o-aminothiophenol. The mixture is stirred at 0° for 2 hours and then diluted with aqueous sodium bicarbonate solution and dichloromethane to adjust the pH to 7.5–8.0. The aqueous layer is extracted twice with dichloromethane, cooled in an ice-water bath, and then acidified to pH4. The resulting precipitate is collected, washed with acetone:water (1:1) and then acetone, and finally dried to give the desired product, 6β-aminopenicillanic acid.

Similarly, the deacylation process of Examples 1 to 7 can be performed by substituting an equivalent amount of

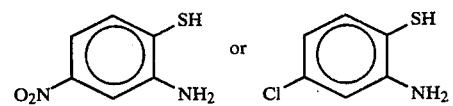

for the o-aminothiophenol.

What is claimed is:

1. A process for removing the acyl sidechain from cephalosporins and penicillins of the formula

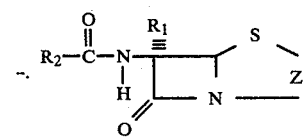

wherein Z is

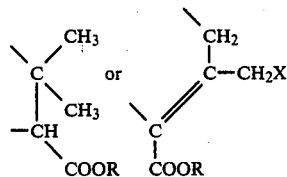

R is a readily removable carboxy protecting group; $R_1$ is in the α-configuration and is hydrogen or methoxy; X is hydrogen, acetoxy, or —S-hetero; $R_2$ is straight or branched chain lower alkyl of 1 to 4 carbons, benzyl, phenoxymethyl, —(CH$_2$)$_3$—COOR

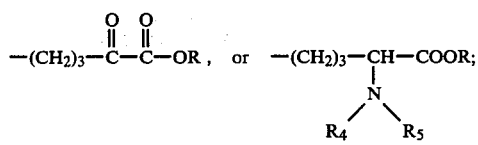

is hydrogen and $R_5$ is an amino protecting group or $R_4$ and $R_5$ taken together with the N-atom are succinimido or phthalimido; which comprises treating said acylated compound with a chlorinating agent and then treating the resulting iminochloride with an o-aminothiophenol of the formula

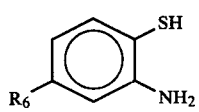

wherein $R_6$ is hydrogen, nitro, or chloro, to yield the deacylated product of the formula

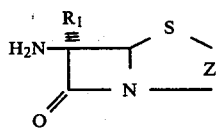

2. The process of claim 1 wherein Z

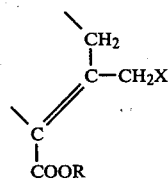

3. The process of claim 2 wherein $R_6$ is hydrogen.
4. The process of claim 3 wherein $R_1$ is methoxy; X is

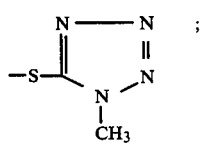

-continued
$R_2$ is —(CH$_2$)$_3$—CH—COOR;
   |
   NH
   |
   $R_5$

R is benzhydryl; and $R_5$ is

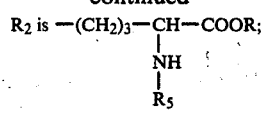

5. The process of claim 3 wherein $R_1$ is methoxy; X is

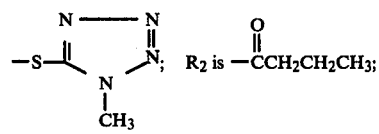

and R is benzhydryl.
6. The process of claim 3 wherein $R_1$ is hydrogen; X is hydrogen; $R_2$ is benzyl; and R is 2,2,2-trichloroethyl.
7. The process of claim 3 wherein $R_1$ is hydrogen; X is hydrogen; $R_2$ is benzyl; and R is —Si(CH$_3$)$_3$.
8. The process of claim 3 wherein $R_1$ is methoxy; X is acetoxy; $R_2$ is benzyl; and R is t-butyl.
9. The process of claim 1 wherein Z is

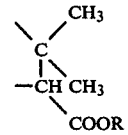

10. The process of claim 9 wherein $R_6$ is hydrogen.
11. The process of claim 10 wherein $R_1$ is hydrogen; $R_2$ is benzyl; and R is 2,2,2-trichloroethyl.
12. The process of claim 10 wherein $R_1$ is hydrogen; $R_2$ is benzyl; and R is —Si(CH$_3$)$_3$.
13. A process for removing the acyl sidechain from iminochloride cephalosporins and penicillins of the formula

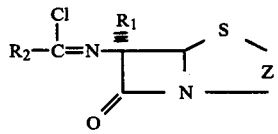

wherein Z is

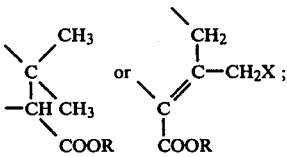

R is a readily removable carboxy protecting group; $R_1$ is in the α-configuration and is hydrogen or methoxy; X is hydrogen, acetoxy, or —S-hetero; $R_2$ is straight or branched chain lower alkyl of 1 to 4 carbons, benzyl, phenoxymethyl, —(CH$_2$)$_3$—COOR,

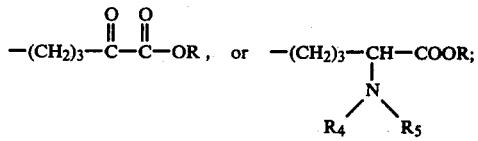

R4 is hydrogen, and R5 is an amino protecting group or R4 and R5 taken together with the N-atom are succinimido or phthalimido; which comprises treating said iminochloride with an o-aminothiophenol of the formula

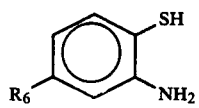

wherein R6 is hydrogen, nitro, or chloro to yield the deacylated product of the formula

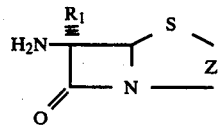

14. The process of claim 13 wherein Z is

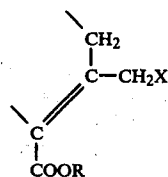

15. The process of claim 14 wherein R6 is hydrogen.
16. The process of claim 15 wherein $R_1$ is methoxy; X is

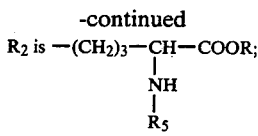

-continued
$R_2$ is

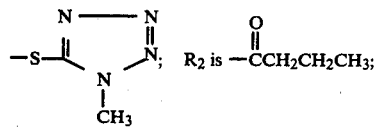

R is benzhydryl; and $R_5$ is

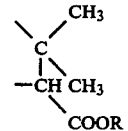

17. The process of claim 15 wherein $R_1$ is methoxy; X is $-S-\underset{\underset{CH_3}{|}}{\underset{N}{\overset{N=\!\!=\!\!N}{\diagdown\!\!\diagup}}}$ ; $R_2$ is $-\overset{O}{\overset{\|}{C}}CH_2CH_2CH_3$;

and R is benzhydryl.

18. The process of claim 15 wherein $R_1$ is hydrogen; X is hydrogen; $R_2$ is benzyl; and R is 2,2,2-trichloroethyl.

19. The process of claim 15 wherein $R_1$ is methoxy; X is acetoxy; $R_2$ is benzyl; and R is t-butyl.

20. The process of claim 15 wherein $R_1$ is hydrogen; X is hydrogen; $R_2$ is benzyl; and R is $-Si(CH_3)_3$.

21. The process of claim 13 wherein Z is $\begin{array}{c} \diagdown\!\!\diagup CH_3 \\ C \\ -CH\diagdown CH_3 \\ \diagdown COOR \end{array}$ 22. The process of claim 21 wherein $R_6$ is hydrogen.
23. The process of claim 22 wherein $R_1$ is hydrogen; $R_2$ is benzyl; and R is 2,2,2-trichloroethyl.
24. The process of claim 21 wherein $R_1$ is hydrogen; $R_2$ is benzyl; and R is $-Si(CH_3)_3$.
25. The process of claim 1 wherein said o-aminothiophenol is provided in an amount which is from equimolar to a molar excess of said iminochloride.
26. The process of claim 25 wherein said treating with said o-aminothiophenol is at $-35°$ C. to $35°$ C.
27. The process of claim 13 wherein said o-aminothiophenol is provided in an amount which is from equimolar to a molar excess of said iminochloride and said treating with said o-aminothiophenol is at $-35°$ C. to $35°$ C.

* * * * *

UNITED STATES PATENT AND TRADEMARK OFFICE
CERTIFICATE OF CORRECTION

PATENT NO. : 4,252,973
DATED : February 24, 1981
INVENTOR(S) : William A. Slusarchyk, et al.

It is certified that error appears in the above-identified patent and that said Letters Patent are hereby corrected as shown below:

Col. 5, line 49, "in vacuo" should be italicized.

Col. 5, lines 50 and 51, "in vacuo" should be italicized.

Col. 7, line 15, "in vacuo" should be italicized.

Col. 8, after "(DCCl$_3$)" the "∿" should read -- $\delta$ --.

Col. 9, line 20 after the last formula, add -- $R_4$ --.

Signed and Sealed this

Twentieth Day of October 1981

[SEAL]

Attest:

GERALD J. MOSSINGHOFF

*Attesting Officer*   *Commissioner of Patents and Trademarks*